United States Patent
Takemoto et al.

(10) Patent No.: US 9,895,375 B2
(45) Date of Patent: Feb. 20, 2018

(54) COMPOSITIONS CONTAINING RIBOFLAVIN AND SESAMIN-CLASS COMPOUNDS

(71) Applicant: SUNTORY HOLDINGS LIMITED, Osaka (JP)

(72) Inventors: Daisuke Takemoto, Osaka (JP); Norifumi Tateishi, Osaka (JP); Yoshiko Ono, Osaka (JP); Kayo Saito, Osaka (JP); Akifumi Maeda, Osaka (JP)

(73) Assignee: SUNTORY HOLDINGS LIMITED, Osaka-shi, Osaka (JP)

(*) Notice: Subject to any disclaimer, the term of this patent is extended or adjusted under 35 U.S.C. 154(b) by 0 days.

(21) Appl. No.: 14/551,188

(22) Filed: Nov. 24, 2014

(65) Prior Publication Data

US 2015/0080407 A1 Mar. 19, 2015

Related U.S. Application Data

(62) Division of application No. 12/282,707, filed as application No. PCT/JP2007/005270 on Mar. 15, 2007, now abandoned.

(30) Foreign Application Priority Data

Mar. 15, 2006 (JP) ................................ 2006-070487

(51) Int. Cl.
| | |
|---|---|
| A61K 31/343 | (2006.01) |
| A61K 31/525 | (2006.01) |
| A23L 2/52 | (2006.01) |
| A61K 31/34 | (2006.01) |
| A61K 31/36 | (2006.01) |
| A23L 33/105 | (2016.01) |
| A23L 33/15 | (2016.01) |

(52) U.S. Cl.
CPC .............. A61K 31/525 (2013.01); A23L 2/52 (2013.01); A23L 33/105 (2016.08); A23L 33/15 (2016.08); A61K 31/34 (2013.01); A61K 31/343 (2013.01); A61K 31/36 (2013.01); A23V 2002/00 (2013.01)

(58) Field of Classification Search
CPC ...... A61K 31/34; A61K 31/36; A61K 31/343; A61K 31/525
See application file for complete search history.

(56) References Cited

U.S. PATENT DOCUMENTS

| | | | |
|---|---|---|---|
| 4,427,694 A | 1/1984 | Benecke et al. | |
| 5,180,588 A | 1/1993 | Shinmen et al. | |
| 5,211,953 A | 5/1993 | Shinmen et al. | |
| 5,637,610 A * | 6/1997 | Nakabayashi | A23L 1/0315 514/458 |
| 5,814,632 A | 9/1998 | Araki et al. | |
| 5,945,420 A | 8/1999 | Araki et al. | |
| 5,948,451 A | 9/1999 | Igarashi | |
| 5,993,795 A | 11/1999 | Osawa et al. | |
| 6,159,507 A | 12/2000 | Igarashi | |
| 6,172,106 B1 * | 1/2001 | Forse | A61K 31/36 514/464 |
| 7,396,554 B2 * | 7/2008 | Jayalekshmy | A23D 9/06 426/451 |
| 7,427,619 B2 * | 9/2008 | Burzynski | A61K 31/195 514/251 |
| 2002/0039599 A1 | 4/2002 | Lin et al. | |
| 2004/0033252 A1 | 2/2004 | Yamamoto et al. | |
| 2004/0059110 A1 | 3/2004 | Nakano et al. | |
| 2005/0158424 A1 | 7/2005 | Nakano et al. | |
| 2005/0256031 A1 * | 11/2005 | Hageman | A23L 1/296 514/23 |
| 2006/0058376 A1 | 3/2006 | Moritani et al. | |
| 2006/0115556 A1 | 6/2006 | Foulger et al. | |
| 2008/0020033 A1 | 1/2008 | Kawashima et al. | |
| 2009/0054443 A1 | 2/2009 | Takemoto et al. | |
| 2009/0092733 A1 | 4/2009 | Nakai et al. | |
| 2009/0169682 A1 | 7/2009 | Okumura et al. | |
| 2010/0048695 A1 | 2/2010 | Ono et al. | |

FOREIGN PATENT DOCUMENTS

| | | |
|---|---|---|
| CN | 1836555 A | 9/2006 |
| EP | 0524796 A1 | 1/1993 |
| EP | 0627213 A1 | 12/1994 |
| EP | 2 090 302 A1 | 8/2009 |
| EP | 2 135 606 A1 | 12/2009 |
| JP | 03-053866 A | 3/1901 |
| JP | 04-9331 | 1/1992 |
| JP | 4-278067 A | 10/1992 |
| JP | 5-51388 | 3/1993 |

(Continued)

OTHER PUBLICATIONS

Japanese Application No. 2014-114790—Office Action dated Jan. 5, 2016 (with partial English translation).

(Continued)

*Primary Examiner* — Zohreh A Fay (74) *Attorney, Agent, or Firm* — Drinker Biddle & Reath LLP (57) ABSTRACT

The present invention relates to a composition containing riboflavin and a sesamin-class compound(s). This composition may incorporate a sesamin-class compound(s) in such an amount that the proportion (weight ratio) of its total quantity to the total quantity of riboflavin taken as unity is no more than 4.5, and it has the advantage that the analgesic and anti-fatigue actions of riboflavin are synergistically improved by ingestion of riboflavin in combination with a sesamin-class compound(s). The composition of the present invention provides compositions, in particular, pharmaceuticals as well as foods and beverages that are safe to humans, animals, etc., and can therefore be ingested for a continued period, and which have far superior effects to those of conventional foods having an analgesic or anti-fatigue action.

4 Claims, 3 Drawing Sheets

(56) References Cited

FOREIGN PATENT DOCUMENTS

| | | |
|---|---|---|
| JP | 5-058902 A | 3/1993 |
| JP | H05-051388 A | 3/1993 |
| JP | 5-201864 A | 8/1993 |
| JP | H05194244 | 8/1993 |
| JP | 06227977 A | 8/1994 |
| JP | 6-327435 | 11/1994 |
| JP | 07-059540 | 3/1995 |
| JP | 8-26987 | 1/1996 |
| JP | 8-47381 | 2/1996 |
| JP | 9-124473 | 5/1997 |
| JP | 10-029941 A | 2/1998 |
| JP | H10218785 A | 8/1998 |
| JP | 2001-046021 A | 2/2001 |
| JP | 2001-139579 A | 5/2001 |
| JP | 2003146844 A | 5/2003 |
| JP | 2003-183172 A | 7/2003 |
| JP | 2004-189619 A | 7/2004 |
| JP | 2004-345988 A | 12/2004 |
| JP | 2005-023008 A | 1/2005 |
| JP | 2007-008878 A | 1/2007 |
| JP | 2008-136391 A | 6/2008 |
| JP | 2008-285463 A | 11/2008 |
| KR | 2001-0029185 A | 4/2001 |
| KR | 2002-0090077 | 11/2002 |
| WO | WO-1997-001968 A1 | 1/1997 |
| WO | WO-03045372 A1 | 6/2003 |
| WO | WO-2004/110175 A1 | 12/2004 |
| WO | WO-2005/054415 A1 | 6/2005 |
| WO | WO-2007/004570 A1 | 1/2007 |
| WO | WO-2007/043656 A1 | 4/2007 |
| WO | WO-2007/105757 A1 | 9/2007 |
| WO | WO-2007/119378 A1 | 10/2007 |
| WO | WO-2008/007728 A1 | 1/2008 |
| WO | WO-2008/062559 A1 | 5/2008 |
| WO | WO-2008/126587 A1 | 10/2008 |

OTHER PUBLICATIONS

Cho-ri kagaku, cookery Science, 1987, vol. 20, No. 1, pp. 9-19 (with partial English translation).
International Search Report dated Dec. 16, 2008 in International Application No. PCT/JP2008/066767 filed Sep. 17, 2008.
Extended European Search Report in European Application No. 08832483.5 dated Sep. 13, 2010.
Suja, et al., "Free Radical Scavenging Behavior of Antioxidant Compounds of Sesame (Sesamum indicum L.) in DPPH• System", J. Agric. Food Chem., 2004, vol. 52, pp. 912-915.
Wu, et al., "Effects of L-Malate on Physical Stamina and Activities of Enzymes Related to the Malate-Aspartate Shuttle in Liver of Mice", Physiol. Res., 2007, 56, pp. 213-220.
European Search Report in EP Application 14184312.8, dated Dec. 23, 2014.
Fukuda et al. "Recent Studies on Sesame Seed and Oil," Nippon Shokuhin Kogyo Gakkaishi, vol. 35, No. 8, 1988, pp. 552-562.
Hiramoto et al. "Sanka Stress to Hiro," Journal of Clinical and Experimental Medicine, Feb. 2003, vol. 204, No. 5, pp. 309-313.
Kataoka, "Sanka Stress to No no Hiro," Journal of Clinical and Experimental Medicine, Feb. 2003, vol. 204, No. 5, pp. 314-318.
Singh et al. "Role of Antioxidants in Chronic Fatigue Syndrome in Mice," Indian Journal of Experimental Biology, Nov. 2002, vol. 40, No. 11, pp. 1240-1244.
Inoue et al. "Hirou no Kagaku (Science on Fatigue)," published by Kodansha on May 20, 2001, pp. 222-228.
Kodama et al. "The Value of the Dehydroepiandrosterone-Annexed Vitamin C Infusion Treatment in the Clinical Control of Chronic Fatigue Syndrome (CFS). II. Characterization of CFS Patients with Special Reference to their Response to a New Vitamin C Infusion Treatment," In Vivo, Nov.-Dec. 1996, vol. 10, No. 6, pp. 585-596.
International Search Report dated Jun. 17, 2008 in International PCT Application PCT/JP2008/054466 filed Mar. 12, 2008.

Keenoy et al., "Antioxidant status and lipoprotein peroxidation in chronic fatigue syndrome," Life Sciences 68 (2001), pp. 2037-2049.
Patent Examination Report No. 2 dated Aug. 6, 2013, by the Australian Government in Australian Patent Application No. 2008239318.
Mohammad Akmal Khan, "Hab Hindi," Qaraabaadeen Azam wa Akmal (20th century AD), Matba Siddiqi, Delhi / Matba Mustafai, Delhi, 1909. (TKDL Abstract No. BA3/502).
P.V. Sharma (e.d.), "Tila Taila Prayoga," Sodhalanighantauh—(Namasamgraha Va Gunasamgraha), Oriental Institute, Baroda, 1st. Edition, 1978. (TKDL Abstract No. RG9/584B).
Therayar Kappiyam (e.d.), "Ellu Gunam", Dr. Anandakumar, Chennai, 1975. (TKDL ABstract No. SR06/116A).
P.V. Sharma (e.d.), "Tilagunah," Dhanvantarinighantauh, Chaukhambha Orientalia, Varanasi, 3rd edition, 2002. (TKDL Abstract No. AK12/482).
Therayar Maha Karisal (e.d.), "Ellu Karpam," Dr. R. Thiyagarajan, Pandit S.S. Anandam Anbu Selvi Pres, Chennai, 1974. (TKDL Abstract No. GP04/135S).
Zhou et al., "Magic Sesamin," Anhui Science & Technology, No. 9, p. 48 (2003) (in Chinese with partial English translation).
Cui Yun-shan, et al., "Pharmacological study on anti-aging effects of Seam in Powders", Journal of Jilin University, vol. 31, No. 3, May 2005, pp. 411-413 and 419 (partial English translation).
Extended European Search Report for Application No. EP 08721882.2, dated May 15, 2014.
Nishibe et al., "Phenolic Compounds from Stem Bark of Acanthopanax senticosus and Their Pharmacological Effect in Chronic Swimming Stressed Rats", Chemical and Pharmaceutical Bulletin, Pharmaceutical Society of Japan, vol. 38, No. 6, (Jan. 1, 1990) pp. 1763-1765.
Sodhala, "Tial Taila Prayoga", TKDL, P.V. Sharma, Oriental Institute, Baroda, (Jan. 1, 1978).
Singh et al., "Effect of Natural and Synthetic Antioxidants in a Mouse Model of Chronic Fatigue Syndrome", Journal of Medicinal Food, vol. 5, No. 4, (Dec. 1, 2002), pp. 211-220.
Logan et al., "Chronic fatigue syndrome: oxidative stress and dietary modifications", Alternative Medicine Review, vol. 6, No. 5, (Oct. 1, 2001), pp. 450-459.
Han et al., "Studies on the Antioxidant Components of Korean Ginseng (IV)—Antifatigue Active Components -", Yakhakhoe-Chi / Taehan Yakhakhoe, Korean Intellectual Property Office, vol. 28, No. 4, (Aug. 30, 1984), pp. 231-235.
Ikeda et al., "Protective effect of sesamin administration on exercise-induced lipid peroxidation.", International Journal of Sports Medicine, vol. 24, No. 7, (Oct. 2003), pp. 530-534.
Kiso et al., "Antioxidative effects of sesamin during high intensity exercise", Medicine and Science in Sports and Exercise, vol. 35, No. 5 Supplement, 1489, (May 2003), p. S269, and at the 50th Annual Meeting of the American College of Sports Medicine; San Francisco, CA, USA; (May 28-31, 2003).
International Search Report dated Dec. 16, 2008 in International Application No. PCT/JP2008/066772 filed Sep. 17, 2008.
El-Arab et al., "Vitamin B1 profile of the Egyptian core foods and adequacy of intake", Food Compos. Anal 17, pp. 81-97, (2004).
Moriura et al., "Pharmacological Study on Agkistrodon blomhoffii blomhoffii BOIE. V.1) Anti-fatigue Effect of the 50% Ethanol Extract in Acute Weight-Loaded Forced Swimming-Treated Rats", Biol. Pharm. Bull. 19(1), pp. 62-66, (1996).
Ide et al., "Interaction of dietary fat types and sesamin on hepatic fatty acid oxidation in rats", Biochim. Biophys. Acta. 1682, pp. 80-91, (2004).
Webpage of http://www.doh.gov.tw/ufile/doc/A00083 (published Oct. 3, 2006) (with English translation).
Webpage of http://pure17go.youthwant.com.tw/item_id9987.htm (published Apr. 15, 2000) (with English translation).
Puri, "The use of eicosapentaenoic acid in the treatment of chronic fatigue syndrome", Prostaglandins, Leukotrienes and Essential 70, pp. 399-401 (2004).
Liu et al., "Determination of Fatty Acid Levels in Erythrocyte Membranes of Patients with Chronic Fatigue Syndrome", Nutr Neurosci 9 (6), pp. 389-392 (2003).

(56) References Cited

OTHER PUBLICATIONS

Hemalatha et al., "Lignans and Tocopherols in Indian Sesame Cultivars", JAOCS 81(5), pp. 467-470 (May 2004).
Shoichi et al., JP63-044843A, published Feb. 25, 1988, Machine Translation used for the Office Action.
Puri BK. Long-chain polyunsaturated fatty acids and the pathophysiology of myalgic encephalomyellitis (chronic fatigue syndrome). J. Clin. Pathol. 2007; 60: 122-24.
Life Extention. Datasheet [online]. LEM, last modified Oct. 30, 2005 [retrieved on May 14, 2013]. Retrieved from the Internet: <URL: <http://supple.s166.xrea.com/pukiwiki/index.php?cmd=read&page=LEM>.
Life Extension Vitamins. Datasheet [online]. Wayback Machine, published Feb. 9, 2006 [retrieved May 15, 2013]. Retrieved from the Internet: <URL: <http://web.archive.org/web/20060209001438/http://www.lifeextensionvitamins.com/liexmixtawex1.html>.
Chronic Fatigue Syndrome. Datasheet [online]. Wayback Machine, published Sep. 8, 2004, [retrieved May 15, 2013]. Retrieved from the Internet: <URL: <http://web.archive.org/web/20040908225030/http://lifeextensionvitamins.com/chfasysu.html>.
Duhoon et al., "Medicinal and Curative Properties of Sesame (*Sesamum Indicum* L.)," J. Econ. Taxon. Bot. vol. 27, No. 1 (2003), pp. 20-28.
Supplemental European Search Report dated Apr. 18, 2012, in EP application No. 07738720.7.
Sesame (Sesamin), http://www1.u-netsurf.ne.jp/~g-time/health/health_2-1.html, Nov. 3, 2005, and an excerpted English translation thereof (cited in the Japanese Official Action dated Sep. 18, 2012).
Franca et al., "B Vitamins Induce an Antinociceptive Effect in the Acetic Acid and Formaldehyde Models of Nociception in Mice," European Journal of Pharmacology, (2001), vol. 421, pp. 157-164.
Schoenen et al., "Effectiveness of High-Dose Riboflavin in Migraine Prophylaxis," Neurology, (Feb. 1998), vol. 50, pp. 466-470.
Granados-Soto et al., "Riboflavin Reduces Hyperalgesia and Inflammation But Not Tactile Allodynia in the Rat," European Journal of Pharmacology, (2004), vol. 492, pp. 35-40.
International Search Report dated Apr. 17, 2007 in PCT/JP2007/055270 filed Mar. 15, 2007.

* cited by examiner

COMPOSITIONS CONTAINING RIBOFLAVIN AND SESAMIN-CLASS COMPOUNDS

This is a Divisional of co-pending application Ser. No. 12/282,707, filed Sep. 12, 2008, which is a PCT National Stage application of PCT/JP2007/1055270 filed Mar. 15, 2007, which claims priority to JP Application No. 2006-070487 filed Mar. 15, 2006.

TECHNICAL FIELD

The present invention relates to compositions that can potentiate the physiological activities of riboflavin and which contains both riboflavin and a sesamin-class compound(s); more particularly, the invention relates to compositions having an analgesic action that can prevent and/or reduce the pain due to a variety of diseases and trauma, or to compositions having an anti-fatigue action that can prevent and/or alleviate physical and/or mental fatigue, as well as foods and beverages that contain such compositions.

BACKGROUND ART

Riboflavin, also known as vitamin $B_2$ is a physiologically active substance that is classified as a water-soluble type of vitamin. This riboflavin is said to aid in preventing and treating many eye diseases including cataracts, sometimes ameliorating symptoms such as inflammation, drying or itching of the eye, and eye strain. As for the physiological activities of riboflavin, it has been reported that riboflavin-containing compounds have an immunolo-augmenting action (Patent Document 1) and that riboflavin-containing compounds are useful as a toxin shock preventing or treating agent (Patent Document 2).

Further reports have been made on the analgesic action of riboflavin as one of its physiological activities. Examples include the following reports: that riboflavin ingested in high doses was effective for migraine prophylaxis (Non-patent Document 1); that riboflavin showed an analgesic action against inflammatory pain in a dose-dependent fashion when it was administered intraperitoneally at concentrations of 3 to 100 mg/kg but it was ineffective against pain in the nervous system (Non-patent Document 2); that when riboflavin was administered perorally at concentrations of 1 to 50 mg/kg, its analgesic effect in a formaldehyde test peaked at 25 mg and did not rise any further even when the dose was increased up to 75 mg (Non-patent Documents 2 and 3).

It has been known that B vitamins including vitamin $B_2$ have anti-fatigue actions, namely, the fatigue relieving and preventing actions of B vitamins are known (Patent Document 3). In addition, supplements and drinks that contain vitamin $B_1$, vitamin $B_2$ and vitamin $B_6$ are commercially available for ingestion by consumers who are fatigued or have rough skin.

[Patent Document 1] JP 5-201864 A
[Patent Document 2] JP 10-29941 A
[Patent Document 3] JP 2005-23008 A
[Non-patent Document 1] Schoenen J., NEUROLOGY, 50, 466-470, 1998
[Non-patent Document 2] European Journal of Pharmacology, 421, 157-164, 2001
[Non-patent, Document 3] European Journal of Pharmacology, 492, 35-40, 2004

DISCLOSURE OF THE INVENTION

Problems to be Solved by the Invention

As described above, various physiological activities of riboflavin have been reported; however, its effects are not necessarily satisfactory and riboflavin is mainly incorporated for the purpose of supplementing the physiological activities of other compounds and no attempt to enhance the physiological activities of riboflavin per se has been suggested or disclosed. In addition, as described above, B vitamins have been known to have the anti-fatigue action but no specific disclosure has been made about the anti-fatigue action of riboflavin (vitamin $B_2$).

An object of the present invention is to provide compositions, in particular, foods and beverages, that are safe to humans, animals, etc. and can therefore be ingested for a continued period and which are capable of potentiating the physiological activities of riboflavin.

Means for Solving the Problems

The present inventors made intensive studies in order to solve the aforementioned problems and found surprisingly that the physiological activities of riboflavin could be potentiated when ingested together with a sesamin-class compound(s). Specifically, as described above, there is an upper limit to the effect of the analgesic action that can be attained by oral administration of riboflavin alone but the present inventors found that the effect of riboflavin was potentiated by ingesting it together with a sesamin-class compound(s) and that riboflavin displayed an analgesic effect that could not be attained by ingesting it alone. In addition, the present inventors assessed riboflavin by a swimming behavior test in a water-immersion stress model animal which is regarded as a model for evaluating the degree of fatigue; as a result, they found that riboflavin has an anti-fatigue action. And the present inventors also found that the anti-fatigue action of riboflavin, when combined with a sesamin-class compound(s), was of such a degree that it could not be attained by ingesting riboflavin alone and that riboflavin and a sesamin-class compound(s) displayed an outstanding synergism. These findings have led to the accomplishment of the present invention.

Thus, the present invention relates to the compositions set forth below that include foods and beverages.

1. A composition containing riboflavin and a sesamin-class compound(s).
2. The composition according to 1 above, wherein, the proportion (weight ratio) of the total quantity of the sesamin-class compound(s) to the total quantity of riboflavin taken as unity is no more than 4.5.
3. The composition according to 1 or 2 above, wherein the sesamin-class compound(s) are a concentrate of a sesamin-class compound(s) which contains at least 1 wt % of a sesamin-class compound(s).
4. The composition according to any one of 1 to 3 above, wherein the sesamin-class compound(s) consist of sesamin and/or episesamin.
5. The composition according to any one of 1 to 4 above, wherein riboflavin is riboflavin sodium phosphate or riboflavin butyrate.
6. The composition according to any one of 1 to 5 above, which is for oral use.
7. An analgesic agent containing riboflavin and a sesamin-class compound(s) as active ingredients.

8. An anti-fatigue agent containing riboflavin and a sesamin-class compound(s) as active ingredients.
9. Use of a sesamin-class compound(s) for improving the physiological activities of riboflavin.

BEST MODE FOR CARRYING OUT THE INVENTION (Riboflavin)
The riboflavin according to the present invention (which is hereinafter sometimes designated, "vitamin $B_2$") covers riboflavin derivatives or pharmacologically acceptable salts thereof. The riboflavin derivatives or pharmacologically acceptable salts thereof specifically include flavin-mononucleotide (FMN), flavin-adenine dinucleotide (FAD), riboflavin tetrafautyrate, riboflavin sodium phosphate (vitamin $B_2$ phosphate ester), mono- or diethanolamine salt of riboflavin phosphate, riboflavin butyrate (vitamin $B_2$ butyrate ester), leucoflavin, monohydroflavin, leucoflavin phosphate ester, leucoflavin-mononucleotide, leucoflavin-adenine dinucleotide, etc. Among these, highly absorbable riboflavin sodium phosphate and highly stable riboflavin butyrate are used with advantage. In the present invention, either one or more of the aforementioned riboflavins can be used. In addition, these are in no way limited in terms of the process for producing them and any products selected from among natural extracts, ferments by microorganisms, and synthetics may be used.
(Sesamin-class compound(s))
The sesamin-class compound(s) according to the present invention cover both sesamin and its analogs. The sesamin analogs include not only episesamin but they may also include the dioxabicyclo[3.3.0]octane derivative described in JP 4-9331 A. A sesamin-class compound(s) may specifically be exemplified by sesamin, sesaminol, episesaminol, sesamolin, and the like; although stereoisomers or racemates of these sesamin-class compounds may be used either alone or in admixture, sesamin and/or episesamin can be used with advantage in the present invention. In addition, as long as the desired effects of the present invention are exhibited, metabolites of a sesamin-class compound(s) (such as those described in JP 2001-139579 A) are also sesamin analogs covered, by the sesamin-class compound(s) according to the present invention and can therefore be used in the present invention.
The sesamin-class compound(s) to be used in the present invention are in no way limited by their form, the process for their production, and the like. If, for example, sesamin is chosen as a sesamin-class compound(s), sesamin is extracted from sesame oil by a known method (such as the one described in JP 4-9331 A) may commonly be employed (this may be called a sesamin extract or refined sesamin); alternatively, commercially available sesame oil (in liquid form) may be used as such. However, in the case where sesame oil is used, its characteristic flavor may occasionally be evaluated as being organoleptically undesirable; therefore, it is preferred to use the sesamin extract (or refined sesamin) that has been extracted from sesame oil and which is tasteless and odorless. In addition, in the case where sesame oil is used, its sesamin content is so low that when one tries to incorporate a desirable amount of sesamin, the volume of the riboflavin (vitamin $B_2$) containing composition that is prescribed becomes so large per unit dosage that inconveniences in ingestion might occasionally occur. In particular, in the case of formulating for oral administration, the preparation (e.g. capsule) becomes so big that impediments to ingestion occasionally occur. Therefore, even for the reason that the intake can be reduced, it is preferred to use the sesamin extract (or refined sesamin) from sesame oil.
Thus, a sesamin-class compound(s) to be used are preferably a concentrate of a sesamin-class compound(s). The degree of concentration may be set as appropriate for the kinds of the sesamin-class compound(s) to be used and the form of the composition into which they are incorporated; it is usually preferred to employ a concentrate of a sesamin-class compound(s) in which the sesamin-class compound(s) are concentrated to at least 1 wt %. More preferably, the content of sesamin-class compound(s) in the concentrate of sesamin-class compound(s) is at least 20 wt %, even more preferably at least 50 wt %, still more preferably at least 70 wt %, and concentrating (refining) up to 90 wt % or more is optimum.
As described above, the sesamin-class compound(s) to be used in the present invention are either compounds found in conventional foods or analog compounds thereof and, obviously, they excel in terms of safety. This is also clear from the fact that when 7-week old ICR male mice were administered (orally administered) sesamin for a continued period of 2 weeks at a dose of 2.14 g/day/kg, no abnormal symptoms were observed.
The assignees of the subject application already found that the sesamin-class compound(s) to be used in the present invention, in particular, sesamin and/or episesamin, have an autonomic nervous system modulating action (International Publication WO 2004/105749); however, they were entirely unknown to show the actions claimed by the present invention, i.e., an action that potentiates the analgesic action, as well as an anti-fatigue action, and it has been neither disclosed nor suggested that they can potentiate the physiological activities of riboflavin.
(Analgesic Action and Agent)
The present invention is useful as an analgesic agent that prevents and/or reduces the pain in humans and animals, particularly in humans. The term "animals" as used herein refers to industrial animals, pets, and laboratory animals; specifically, industrial animals refers to those animals which are required to be kept for industrial purposes, including livestock such as cattle, horses, pigs, goats, sheep, etc., poultry such as chickens, ducks, quails, turkeys, ostriches, etc., and fishes such as yellowtail, young yellowtail, red sea bream, common, horse mackerel, carp, rainbow trout, eel, etc.; pets refers to so-called pet animals and companion animals, including dogs, cats, marmots, little birds, hamsters, goldfish, etc.; and laboratory animals refers to those animals which are sacrificed for research in such disciplines as medicine, biology, agronomy, pharmacy, etc. and they include mice, rats, guinea pigs, beagles, miniature pigs, rhesus monkeys, crab-eating monkeys, etc.

The analgesic agent of the present invention is intended to combat a broad spectrum of pains, ranging from a transient and slight pain to a chronic unbearable pain. Pain is usually controlled by using analgesics but their effect is not necessarily adequate; if the pain is chronic pain (ache) associated with arthralgia, neuralgia, lumbago, etc., the pain relieving effect of analgesics is just temporary and, what is more, a continued administration of them may often cause side effects such as gastrointestinal disorders, renal disorders, hepatic disorders, etc. In addition, since the pain associated with arthralgia, neuralgia, lumbago, etc, tends to increase with aging, the recent rapid growth of the population of elderly people is increasing social demands for not only mitigating and eliminating pain but also preventing it.

The analgesic agent of the present invention is useful in combating the above-mentioned various kinds of pains and the diseases that involve such pains. The analgesic agent of the present invention, which uses a sesamin-class compound(s) in combination with riboflavin, synergistically potentiates the analgesic action of riboflavin, thereby displaying a superior analgesic action than conventional analgesics. In addition, its active ingredients are riboflavin and a sesamin-class compound(s) which have been ingested for many years in the form of foods or beverages, so it has no side effects and can be ingested for a continued period. Therefore, it is a new type of analgesic agent which is not only suitable for regular ingestion in order to reduce chronic pain but which can also prevent disease that involves pain (e.g., dysmenorrhea). This may qualify the analgesic agent of the present invention as a useful drug in view of the circumstances under which the sense of pain differs between a highly sensitive person and a less sensitive person and in the absence of an objective scale, it is often difficult to make a clear distinction between a normal state and a diseased state, and it has been desired that the conventional therapeutic act which involves administering medications such as analgesics should be replaced by foods and beverages in forms that can be ingested regularly.

(Anti-fatigue Action and Agent)

The composition of the present invention, in addition to exhibiting the above-described analgesic action, is useful as an anti-fatigue agent in humans and animals. The term "animals" as used herein refers to those animals to which the above-described analgesic agent is to be applied and, in particular, the anti-fatigue agent of the present invention is used in industrial animals, pets, and laboratory animals that perceive pain and it is used in humans with particular advantage. The term "industrial animals" refers to livestock such as cattle, horses, pigs, goats, sheep, etc., as well as racing horses, hunting dogs, etc.; pets refers to dogs, cats, etc.; and laboratory animals refers to those animals which are sacrificed for research in such disciplines as medicine, biology, agronomy, pharmacy, etc. and they include mice, rats, guinea pigs, beagles, miniature pigs, rhesus monkeys, crab-eating monkeys, etc.

Fatigue is a temporary decrease in both physical and mental performances that is observed when a physical and a mental stress is applied continuously and the decreased performance means a qualitative or quantitative drop in the capacity for physical and metal work. In addition, the term "fatigue" as used in the present invention snail cover chronic fatigue syndrome and death from overwork.

The anti-fatigue agent of the present invention has the action of attenuating the above-defined fatigue or restoring from such fatigue; specific examples include the actions of prolonging the rime of duration for which an exercising or operating site (including the brain) works, and suppressing the increase of a fatigue-inducing substance in response to the same amount of exercise or operation (improving endurance or enhancing physical strength) and improving such a condition that the brain or nerves are in a state of sensing fatigue although an exercising or operating site has not been fatigued, as well as promoting the recovery from the fatigued state of an exercising or operating site to the normal state.

The chronic fatigue syndrome to be combated by the anti-fatigue agent of the present invention means fundamental symptoms such as a feeling of systemic fatigue, a feeling of weariness, mild fever, swollen lymph nodes, muscular pain, arthralgia, psychoneurotic symptoms, etc. that last for such a prolonged period as to cause impediments in daily life. The anti-fatigue agent of the present invention can treat this chronic fatigue syndrome, namely, palliate the respective symptoms of chronic fatigue syndrome and bring them into the normal state. Further, the death from overwork which is to be combated by the anti-fatigue agent of the present invention means such a condition that although the subject is in a seriously strained state and unable to maintain the physical vigor, the subject is no longer capable of reasonably sensing the fatigue and consequently manifests a cardiovascular disease or cardiac disease to result in permanent disability to work or even death. The anti-fatigue agent of the present invention can treat chronic fatigue syndrome and can thereby prevent death from overwork.

The anti-fatigue effect according to the present invention, or the effect as the "anti-fatigue agent", may typically be confirmed by the following test. That is, by measuring the swimming time in a water-immersion sleep deprivation test. A mouse, kept in such an environment as water immersion that they are unable to have a sufficient sleep or resting position to rest physically or mentally, is forced to swim under the stress of a weight and the time it takes to have its nose submerged in the water for at least 10 seconds is measured to determine the degree of its fatigue. Since this animal model is a physical and mental fatigue model, if the administration of a test substance prolongs the swimming time, it is confirmed that the model has resistance to fatigue, as exemplified by prevention or amelioration of physical and mental fatigue and the accompanying distress such as muscular pain, an increase in physical strength that helps prolong the time to exhaustion, and maintenance of physical vigor in a fatigued state.

The anti-fatigue agent of the present invention, if ingested by humans or animals, makes them less fatigable, and it is also effective in relieving fatigue (recovery from fatigue). Stated more specifically, if physical fatigue is felt during muscular exercise such as sports or if mental fatigue is felt during a continuous operation such as accounting work, the anti-fatigue agent of the present invention may of course be ingested to relieve the fatigue. What is more, if it is ingested in advance before working or playing sports, prevention of fatigue can also be realized. In addition, if it is ingested before or during playing sports, an improvement of endurance is expected. Furthermore, if it is ingested regularly, mental fatigue and the accompanying disease can also be prevented.

(Composition Containing Riboflavin and a Sesamin-class Compound(s))

According to the present invention, a sesamin-class compound(s) are contained in riboflavin, thereby synergistically potentiating the physiological activities of riboflavin, such as analgesic and anti-fatigue actions; at the same time, if the combination is utilized as health food, the physiological actions of the respective components combine to contribute to health promotion.

In the composition of the present invention which contains riboflavin and a sesamin-class compound(s), the amounts in which the respective components can be incorporated are not limited if their physiological actions are to be obtained individually. Usually, riboflavin is preferably incorporated in the amount recommended in the Nutritional Requirements of Japanese People as specified by the Ministry of Health, Labor and Welfare; specifically, it is 1.2 mg for adult male and 1.0 mg for adult female per day. In addition, there have been no reports on the maximum upper limit of riboflavin that can be taken without causing health problems, so there is no upper limit for the amount in which it can be incorporated; usually, it is no more than about 100 mg, preferably no more than about 50 mg, for adult per day. As for a sesamin-class compound(s), they are usually incorporated in such amounts that, they range from about 1 to about 200 mg, preferably from about 5 to about 100 mg, for adult per day.

If, on the other hand, a sesamin-class compound(s) are incorporated in riboflavin with a view to potentiating its physiological activities, they are incorporated in such amounts that the proportion of the total quantity of a sesamin-class compound(s) to the total quantity of riboflavin taken as unity, when it is calculated as riboflavin (which is hereinafter designated as "riboflavin equivalent"), is no more than 4.5, preferably no more than 4.0, and more preferably no more than 3.5, in weight ratio. The larger the proportion of a sesamin-class compound(s) to be incorporated, the more potentiated the actions of riboflavin are likely to be; however, no superior synergism is obtained outside the ranges specified above. The lower limit of the amounts of a sesamin-class compound(s) to be incorporated is in no way specified if they are capable of providing the synergism in the desired action such, as an analgesic or anti-fatigue action, and they may be incorporated with reference made to the daily doses listed above. Generally, the proportion of the total quantity of a sesamin-class compound(s) to the total quantity of riboflavin which, when calculated as riboflavin, is taken as unity is at least 0.01, preferably at least 0.5, more preferably at least 0.1, and even more preferably at least 1, in weight ratio.

One of the physiological activities of riboflavin is analgesic action and it was confirmed that when 30 mg of riboflavin sodium phosphate in terms of riboflavin equivalent and 50 or 100 mg of a sesamin-class compound(s) were administered perorally, namely, at a riboflavin, to sesamins weight ratio of 1:1.67 or 1:3.33, the analgesic action of riboflavin sodium phosphate was improved (Examples 1 and 2). The present inventors also confirmed that another physiological activity of riboflavin is anti-fatigue action and it was confirmed that when 25 mg or 50 mg of riboflavin sodium phosphate in terms of riboflavin equivalent and 50 mg of a sesamin-class compound(s) were administered perorally, namely, at a riboflavin to sesamins weight ratio of 1:2 or 1:1, the anti-fatigue action of riboflavin sodium phosphate was improved but that when 10 mg of riboflavin sodium, phosphate in terms of riboflavin equivalent and 50 mg of a sesamin-class compound(s) were administered perorally, namely, at a riboflavin to sesamins weight ratio of 1:5, the anti-fatigue action of riboflavin sodium phosphate was not potentiated (Examples 3 and 4).

When the composition of the present invention is to be utilized as a pharmaceutical composition, it may be administered perorally in such forms as liquid, tablet, granule, powder, capsule, dry syrup, pill and the like, or it may be administered in the form of an injection or the like; the form of its administration can be selected as appropriate for the clinical condition, the state of its progress, and other conditions. In addition, riboflavin (except riboflavin butyrate) which is an active ingredient, in the present invention is water-soluble whereas a sesamin-class compound(s) as the other active ingredient are fat-soluble, so these two ingredients may be ingested in different forms. Specifically, the analgesic action can be obtained by a method in which granules of riboflavin are ingested together with water and, at the same time, soft capsules filled with a sesamin-class compound(s) as they are dissolved in fat or oil are ingested, or by a method in which the granules of riboflavin and the soft capsules of a sesamin-class compound(s) are ingested at different times in accordance with the respective rates of absorption.

In addition, the dose at which the composition of the present invention is administered may also be selected as appropriate for the subject to which it is applied, the clinical condition, the state of its progress, and other conditions such as the form of administration; if it is to be applied perorally to humans (adults) with a view to obtaining the analgesic action and/or the anti-fatigue action, it is generally administered for a continued period at a frequency of about one to three times a day in amounts ranging from about 1 to about 200 mg, preferably from about 2 to about 100 mg.

In the present invention, so long as its intended effect is not impaired, any desired ingredients may be incorporated in addition to riboflavin and a sesamin-class compound(s). For example, not only physiologically active components including vitamins such as vitamin E and vitamin C, minerals, hormones, nutritional ingredients, and flavoring agents, but also emulsifiers, isotonization agents, buffers, solvent promoters, preservatives, stabilizers, antioxidants and the like that are incorporated in the pharmaceutical formulating procedure may be incorporated as appropriate. As described above, the composition of the present invention can be utilized as an analgesic agent and/or an anti-fatigue agent; in addition, since it is believed that various other physiological actions of riboflavin (vitamin $B_2$) and a sesamin-class compound(s) can be exhibited either additively or synergistically, the composition of the present invention can advantageously be utilized not only as the aforementioned pharmaceutical composition but also as health food.

Examples of the health food as used herein include pharmaceutical preparations or foods, such as capsules or tablets, that contain as an active ingredient the composition of the present invention itself which contains riboflavin and a sesamin-class compound(s), as well as functional foods (including foods for specified health use—FOSHU—and qualified FOSHU) that comprise common foods in which the above-mentioned composition of the present invention is incorporated as one component so that various functions such as analgesic and anti-fatigue actions on the living body are imparted to those foods. Further included among the health foods are those which are characterized by having the analgesic action and/or anti-fatigue action and which have labels attached thereto that state they are used for preventing or reducing the pain in the living body or that they mitigate the fatigue of the living body or promote its recovery from fatigue.

The health foods that contain riboflavin and a sesamin-class compound(s) are not particularly limited in their form and they can be prepared in any form like a solid form such as powder, granules or tablets, or a liquid form such as solution, emulsion or dispersion, or a semi-solid form such paste.

EXAMPLES

On the following pages, the present invention is described more specifically by means of test examples and working examples, to which the present invention is by no means limited.

Test Example 1

Analgesic Action of Sesamin-class Compounds

There is no report on the analgesic action of a sesamin-class compound(s). Therefore, the present inventors studied the analgesic action of a sesamin-class compound(s).

A test on analgesic action was conducted by a partly modified version of the acetic acid writhing test of Moon et. al. (Biol. Pharm. Bull. (2005)). The specific test method was as follows. Wistar male rats (5-week old) were purchased from CLEA Japan, Inc. and acclimatized in the test environment for a week; thereafter, the animals that showed normal growth were subjected to the test. Three days before the acetic acid writhing test, the rats were divided into three groups each consisting of 6 heads; the control group was orally administered through a tube with olive oil at a dose of 5 ml/kg whereas the remaining two groups were administered with sesamin-class compounds (sesamin/episesamin mixture; sesamin: episesamin (weight ratio)=5:5) as they were dissolved in olive oil at respective doses of 50 mg/kg and 100 mg/kg. Subsequently, administration was similarly performed two days before the test and on the day before the test, two administrations were effected, one in the morning and the other in the evening; thus, a total of four administrations were effected. On the day of testing, rats that had been fasted overnight from the previous night were orally administered with 5 ml/kg of physiological saline and one hour later, they were administered intraperitoneally with 1 ml/170 g of physiological saline containing 1% acetic acid and immediately after this administration, the number of writhing movements the animals made for 30 minutes right after the administration was counted.

Figure 1:
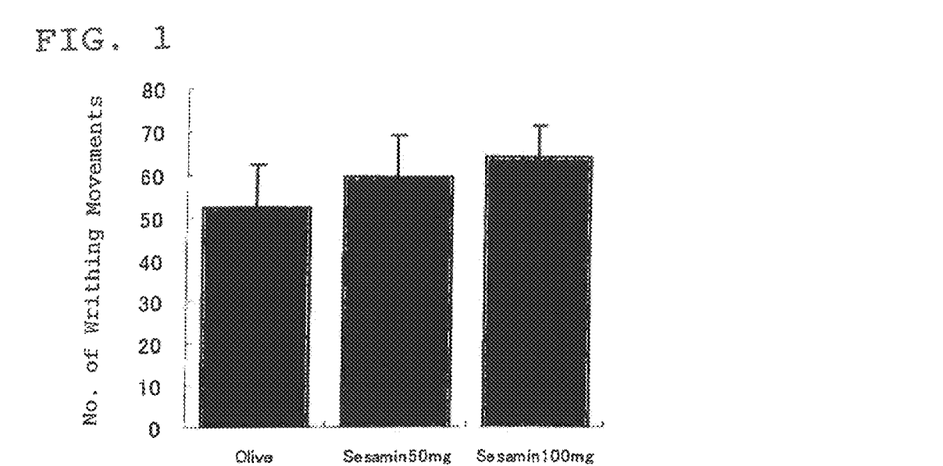
FIG. 1 is a graph showing the effect of sesamin-class compounds on the analgesic action.

The results are shown in FIG. 1. The groups administered with sesamin-class compounds (Sesamin 50 mg, and Sesamin 100 mg) had a tendency to writhe slightly more often than the control group (Olive), making it clear that sesamin-class compounds had no analgesic action in the acetic acid writhing test.

Example 1

Analgesic Action (1) due to Sesamin-class Compounds and Riboflavin (Vitamin $B_2$)

A sesamin-class compound is) were tested for their ability to improve the analgesic action of riboflavin (vitamin $B_2$). Wistar male rats (7-week old) were purchased from CLEA Japan, Inc. and acclimatized in the test environment for a week; thereafter, the animals that showed normal growth were subjected to the test. Three days before the acetic acid writhing test, the rats were divided into four groups each consisting of 6 heads; two groups of them were orally administered through a tube with olive oil at a dose of 5 ml/kg whereas the remaining two groups were administered with the same sesamin-class compounds as used in Test Example 1 as they were dissolved in olive oil (5 ml/kg) at respective doses of 50 mg/kg and 100 mg/kg; as in Test Example 1, a total of four administrations were effected. On the day of testing, rats in the control group that had been fasted overnight from the previous night were orally administered with 5 ml/kg of physiological saline whereas similarly fasted rats in the remaining three groups were orally administered with vitamin $B_2$ (riboflavin sodium phosphate; Nakalai Tesque, Inc.) that was dissolved in physiological saline to give a dose of 30 mg/kg in terms of riboflavin equivalent; then, the number of writhing movements was counted as in Test Example 1.

Figure 2:
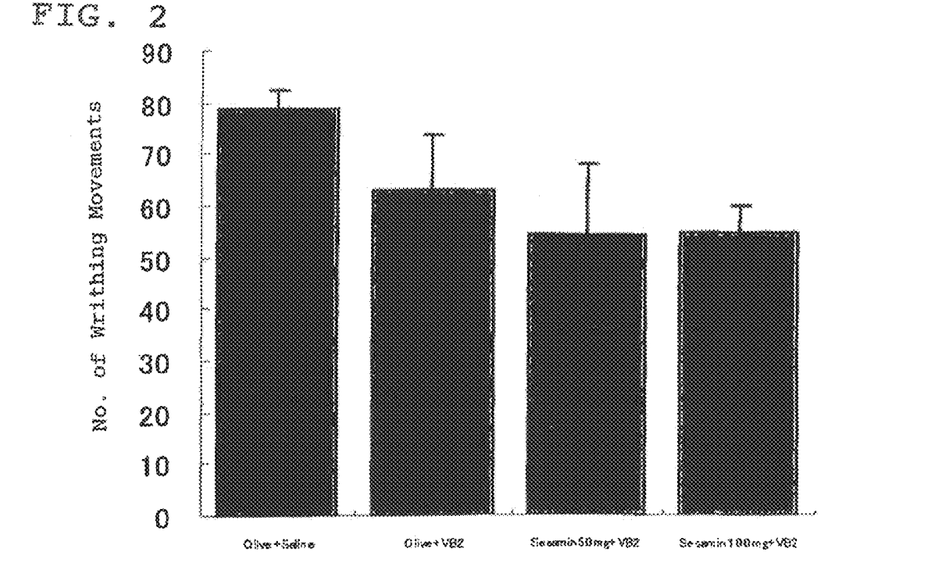
FIG. 2 is a graph showing the analgesic action due to the combination of riboflavin (vitamin $B_2$) and sesamin-class compounds.

The results are shown in FIG. 2. The sole vitamin $B_2$ group (Olive+VB2) showed a tendency to make a smaller number of writhing movements than the control group (Olive+Saline), verifying the analgesic action due to vitamin $B_2$. In comparison with this sole vitamin $B_2$ group (Olive+VB2), the groups of sesamin-class compounds and vitamin $B_2$ in combination (Sesamin 50 mg+VE2, Sesamin 100 mg+VB2) made smaller numbers of writhing movements at the respective sesamins concentrations of 100 mg/kg and 50 mg/kg. It became clear that the analgesic action of vitamin $B_2$ was potentiated by combining it with a sesamin-class compound(s).

Example 2

Analgesic Action (2) due to Sesamin-class Compounds and Riboflavin (Vitamin $B_2$)

Example 1 was checked for its reproducibility. Wistar male rats (7-week old) were purchased from CLEA Japan, Inc. and acclimatized in the test environment for a week; thereafter, the animals that showed normal growth were subjected to the test. Three days before the acetic acid writhing test, the rats were divided into three groups each consisting of 10-18 heads; two groups of them (groups 1 and 2) were orally administered through a tube with olive oil at a dose of 5 ml/kg whereas the remaining two groups (groups 3 and 4) were administered with the same sesamin-class compounds as used in Example 1 as they were dissolved in olive oil (5 ml/kg) at a dose of 100 mg/kg; as in Example 1, a total of four administrations were effected. On the day of testing, rats in two of the four groups (groups 1 and 3) that had been fasted overnight from the previous night were orally administered with 5 ml/kg of physiological saline whereas similarly fasted rats in the remaining two groups (groups 2 and 4) were orally administered with vitamin $B_2$ (riboflavin sodium phosphate; Nakalai Tesque, Inc.) that was dissolved in physiological saline to give a dose of 30 mg/kg in terms of riboflavin equivalent; then, the number of writhing movements was counted as in Test Example 1.

Figure 3:
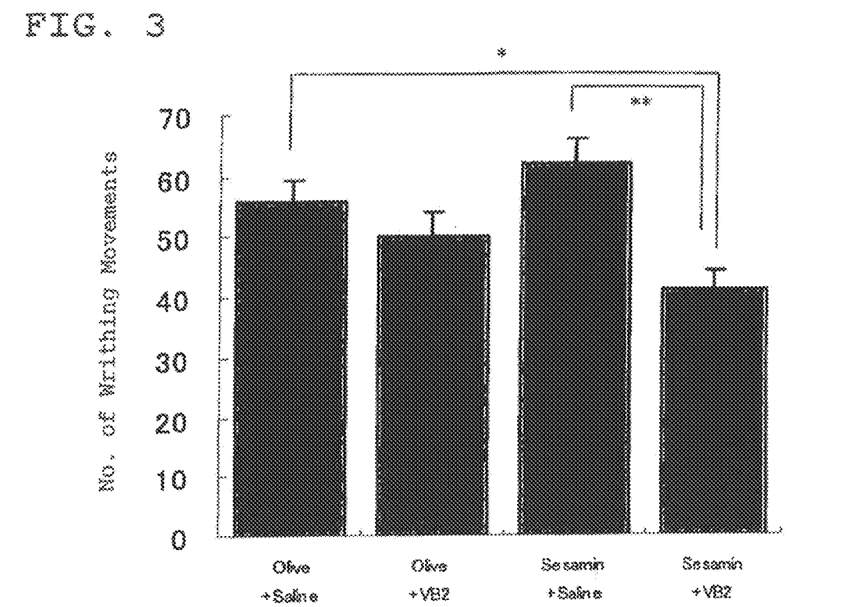
FIG. 3 is a graph showing the synergism in analgesic action due to the combination of riboflavin (vitamin $B_2$) and sesamin-class compounds.

The results are shown in FIG. 3. Compared with the control group (Olive+Saline), the sole vitamin $B_2$ group (Olive+VB2) had a tendency to make a smaller number of writhing movements (10.5% suppression); however, as in Test Example 1, no analgesic action was found in the sole sesamin-class compounds group (Sesamin+Saline). On the other hand, the group of vitamin $B_2$ and sesamin-class compounds in combination (Sesamin+VB2) experienced a considerable decrease in the number of writhing movements (26.6% suppression) and the synergistic analgesic effect due to vitamin $B_2$ and a sesamin-class compound(s) could be confirmed (according to the result of a Tukey multiple comparison test, the risk was $p<0.05$ between the group of vitamin $B_2$ and sesamin-class compounds in combination and the control group, and $p<0.01$ between the group of vitamin $B_2$ and sesamin-class compounds in combination and the sole sesamin-class compounds group).

Example 3

Anti-fatigue Action (1) due to Riboflavin and Sesamin-class Compounds

The test substances, riboflavin and sesamin-class compounds, were respectively the same as in Example 1; in other words, the sesamin/episesamin mixture (sesamin:episesamin (weight ratio)=5:5) and riboflavin (riboflavin sodium, phosphate; Nakalai Tesque, Inc.) were used.

The effect against fatigue was evaluated by a water immersion sleep deprivation test. Evaluation was performed by a partially modified version of the method of Tanaka et al. (Neuroscience Let. 352, 159-162, 2003). To be more specific, eight-week old male Balb/b mice were used as test animals and divided into seven groups as shown in Table 1, each consisting of 9 heads and having the same average body weight. The values of riboflavin given in Table 1 were obtained by calculating as riboflavin the riboflavin sodium phosphate used. Of the seven groups of rats, six were water-immersed, sleep-deprived stress groups, which were kept in cages with floor coverings being replaced by 23° C. tap water that was filled to a depth of 7 mm, so that the mice were immersed in the water to be deprived of sleep. During two days of water-immersed sleep deprivation, the respective test samples were forcibly administered through the mouth for 2 days on a once-a-day basis. Of the two test samples, the sesamin-class compounds were dissolved in olive oil and the riboflavin in distilled water. The order of administration was such that riboflavin was followed by sesamin-class compounds, and the control group was forcibly administered with distilled water and olive oil through the mouth.

After two days of water immersion, the mice were allowed to swim with a weight attached to each of their tails having a mass equivalent to 8% of their body weight, and the time they took to have their nose submerged in water for at least 10 seconds was measured. The mice of the water-immersed group (the water-immersed, sleep deprived stress group) could swim for a shorter period than the mice of the normally kept group and the effect of the test samples against fatigue was determined by seeing how much the shortening of the swimming time could be suppressed in the mice of the test sample administered groups.

TABLE 1

| | |
|---|---|
| Group 1 (cont) Normally kept control group | Distilled water + olive oil |
| Group 2 Water immersed control group | Distilled water + olive oil |
| Group 3 Water immersed riboflavin group | Riboflavin 25.0 mg/kg + olive oil |
| Group 4 Water immersed riboflavin group | Riboflavin 50.0 mg/kg + olive oil |
| Group 5 Water immersed sesamin group | Distilled water + sesamin 50.0 mg/kg |
| Group 6 Water immersed, riboflavin + sesamin group | Riboflavin 25.0 mg/kg + sesamin 50.0 mg/kg |
| Group 7 Water immersed, riboflavin + sesamin group | Riboflavin 50.0 mg/kg + sesamin 50.0 mg/kg |

Figure 4:
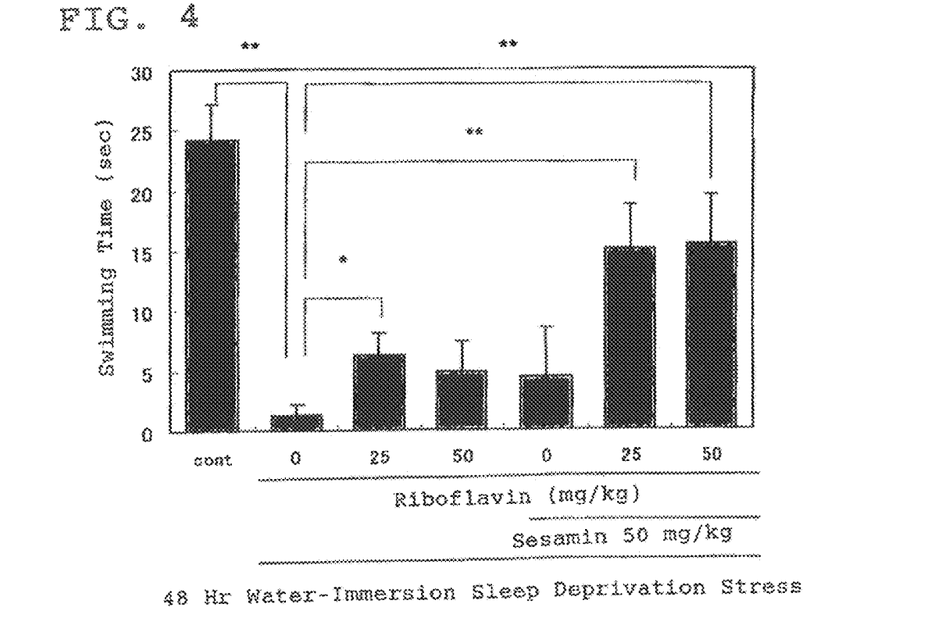
FIG. 4 is a graph showing the anti-fatigue action due to the combination of riboflavin and sesamin-class compounds.

The results are shown in FIG. 4. As is clear from FIG. 4, the water immersed control group could only swim for a shorter time than the normally kept control group. On the other hand, the groups administered with sesamin-class compounds or riboflavin were suppressed in the shortening of the swimming time and the suppressive effect was synergistically potentiated by administering sesamin-class compounds and riboflavin simultaneously.

Example 4

Anti-fatigue Action (2) due to Riboflavin and Sesamin-class Compounds

The anti-fatigue action due to riboflavin and a sesamin-class compound(s) was measured as in Example 3, except that the mice were divided into six groups as shown in Table 2. The values of riboflavin given in Table 2 were obtained by calculating as riboflavin the riboflavin sodium phosphate used.

TABLE 2

| | |
|---|---|
| Group 1 (cont) Normally kept control group | Distilled water + olive oil |
| Group 2 Water immersed control group | Distilled water + olive oil |
| Group 3 Water immersed riboflavin group | Riboflavin 10.0 mg/kg + olive oil |
| Group 4 Water immersed sesamin group | Distilled water + sesamin 50.0 mg/kg |
| Group 5 Water immersed, riboflavin + sesamin group | Riboflavin 10.0 mg/kg + sesamin 50.0 mg/ka |
| Group 6 Water immersed, riboflavin + sesamin group | Riboflavin 50.0 mg/kg + sesamin 50.0 mg/kg |

Figure 5:
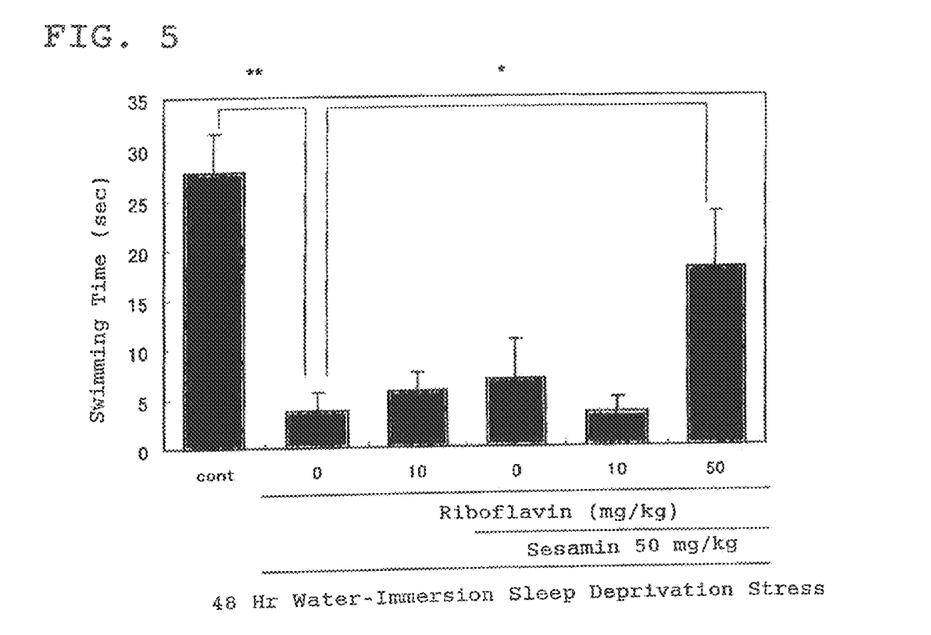
FIG. 5 is a graph showing the anti-fatigue action due to the combination of riboflavin and sesamin-class compounds.

The results are shown in FIG. 5. As is clear from FIG. 5, the synergism of sesamin-class compounds and riboflavin was not exhibited when the former was used at the dose of 50 mg/kg and the latter at the dose of 10 mg/kg. It was suggested that when the synergism was to be obtained, the total quantity of sesamin-class compounds had to be smaller than 5.0 in weight ratio to the total quantity of riboflavin which, when calculated as riboflavin, was taken as unity.

Example 5

Preparations

| (Preparation 1) Granule | |
|---|---|
| Sesamin | 0.01 g |
| Vitamin $B_2$ | 0.01 g |
| Tocopherol acetate | 0.25 g |
| Silicic anhydride | 20.5 g |
| Corn starch | 179.0 g |

The particles of these ingredients were mixed uniformly and 100 ml of a solution having 10% hydroxypropyl cellulose dissolved in ethanol was added, followed by blending, extruding and drying in the usual manner to prepare granules.

| (Preparation 2) Capsule | |
|---|---|
| Gelatin | 60.0% |
| Glycerin | 30.0% |
| Methyl paraoxybenzoate | 0.15% |
| Propyl paraoxybenzoate | 0.51% |
| Water | q.s. |

Into gelatin shells comprising these ingredients, a composition comprising the ingredients shown below was filled to prepare soft capsules each weighing 200 mg.

| | |
|---|---|
| Sesamin | 10.0 mg |
| Vitamin B₂ | 1.0 mg |
| Glyceryl fatty acid ester | 15.0 mg |
| Beeswax | 15.0 mg |
| Wheat germ oil | 250 mg |

| (Preparation 3) Tablet | |
|---|---|
| Sesamin | 0.01 g |
| Vitamin B₂ | 0.01 g |
| Starch | 282 g |
| Sucrose fatty acid ester | 9.0 g |
| Silicon oxide | 9.0 g |

These ingredients were mixed and palletized with a single-action tableting machine to produce tablets each having a diameter of 9 mm and weighing 300 mg.

| (Preparation 4) Drink | |
|---|---|
| Taste component: DL-tartaric acid sodium salt | 0.1 g |
| Succinic acid | 0.009 g |
| Sweetener: Liquid sugar | 800 g |
| Acid ingredient: Citric acid | 12 g |
| Vitamin: vitamin C | 10 g |
| Sesamin | 1 g |
| Vitamin B₂ | 3 g |
| Vitamin E | 3 g |
| Cyclodextrin | 5 g |
| Flavoring agent | 15 ml |
| Potassium chloride | 1 g |
| Magnesium sulfate | 0.5 g |

These ingredients were mixed together and water was added to make a total of 10 liters. The prepared drink would be drunk in a volume of about 100 ml at one time.

INDUSTRIAL APPLICABILITY

The composition of the present invention which contains riboflavin and a sesamin-class compound(s) has the advantage that the physiological activities of riboflavin; for example, analgesic and anti-fatigue actions, are synergistically displayed by ingesting riboflavin in combination with a sesamin-class compound(s); the composition is safe to humans, animals, etc. and can therefore be ingested for a continued period.

The invention claimed is:

1. A method of reducing pain in a subject, comprising: administering a composition containing an effective amount of riboflavin and a sesamin-class compound(s) selected from the group consisting of sesamin, episesamin, sesaminol, episesaminol, and sesamolin to a subject in need thereof, wherein the composition consists essentially of riboflavin and the sesamin class compound(s), and wherein a proportion (weight ratio) of the total quantity of the sesamin-class compound(s) to the total quantity of riboflavin taken as unity in the composition is no more than 4.5.

2. The method according to claim 1, wherein the sesamin-class compound(s) contained in the composition is selected from the group consisting of sesamin and episesamin.

3. A method of reducing fatigue in a subject comprising: administering a composition containing an effective amount of riboflavin and a sesamin-class compound(s) selected from the group consisting of sesamin, episesamin, sesaminol, episesaminol, and sesamolin to a subject in need thereof, wherein the composition consists essentially of riboflavin and the sesamin class compound(s), and wherein a proportion (weight ratio) of the total quantity of the sesamin-class compound(s) to the total quantity of riboflavin taken as unity in the composition is no more than 4.5.

4. The method according to claim 3, wherein the sesamin-class compound(s) contained in the composition is selected from the group consisting of sesamin and episesamin.

* * * * *